United States Patent
Kajiyama

[11] Patent Number: 6,160,403
[45] Date of Patent: Dec. 12, 2000

[54] EVALUATION METHODS AND INSTRUMENTATION WITH STEEL PROBES USED FOR CATHODIC PROTECTION OF UNDERGROUND PIPELINES

[75] Inventor: Fumio Kajiyama, Chiba, Japan

[73] Assignee: Tokyo Gas Company Limited, Japan

[21] Appl. No.: 09/081,804

[22] Filed: May 20, 1998

[30] Foreign Application Priority Data

Jun. 3, 1997 [JP] Japan ................................. 9-145247

[51] Int. Cl.[7] .................................................. G01N 27/42
[52] U.S. Cl. .......................................... 324/425; 324/71.2
[58] Field of Search .................................. 324/425, 71.1, 324/71.2, 700, 713, 72.5, 72, 715

[56] References Cited

U.S. PATENT DOCUMENTS

| | | | |
|---|---|---|---|
| 4,280,124 | 7/1981 | Wuertele | 340/650 |
| 4,437,065 | 3/1984 | Woudstra | 324/425 |
| 4,591,792 | 5/1986 | Birchmeier et al. | 324/425 |
| 5,144,247 | 9/1992 | Speck | 324/425 |
| 5,144,253 | 9/1992 | Blanchard | 324/715 |
| 5,180,968 | 1/1993 | Bruckenstein et al. | 324/71.1 |
| 5,180,969 | 1/1993 | Kwun et al. | 324/71.2 |
| 5,216,370 | 6/1993 | Bushman et al. | 324/425 |
| 5,469,048 | 11/1995 | Donohue | 324/71.1 |
| 5,596,267 | 1/1997 | Lara et al. | 324/71.1 |
| 5,712,559 | 1/1998 | Moore et al. | 324/71.1 |

FOREIGN PATENT DOCUMENTS 8-345313  7/1998  Japan .

OTHER PUBLICATIONS

Japanese Society of Corrosion Engineering, Jun. 5, 1997, Proceedings of JSCE Materials and Environments 1997.

*Primary Examiner*—Safet Metjahic
*Assistant Examiner*—Vincent Q. Nguyen
*Attorney, Agent, or Firm*—McGlew and Tuttle, P.C.

[57] ABSTRACT

A method and a device to assess the adequacy of a cathodically protected underground pipeline with consideration of AC corrosion. A steel probe and a CSE are installed near the pipeline at a depth. The steel probe is electrically connected to a pipeline. The measurements of AC probe currents flowing between a steel probe (2) and the pipeline (1) are per-formed simultaneously with those of on-and off-potentials, and DC probe currents.

7 Claims, 10 Drawing Sheets

Example of recorder output

EVALUATION METHODS AND INSTRUMENTATION WITH STEEL PROBES USED FOR CATHODIC PROTECTION OF UNDERGROUND PIPELINES

FIELD OF THE INVENTION

The present invention relates to evaluation methods and instrumentation with steel probes used for cathodic protection of underground pipelines.

BACKGROUND OF THE INVENTION

It is well known that the adequacy of an underground pipeline cathodic protection system is assessed by measuring off-potential and DC current of a steel probe placed near the pipeline at depth (i.e., in the same environmental conditions). A saturated copper/copper sulfate reference electrode (CSE) is also installed in the vicinity of the steel probe. The steel probe, simulating a coating defect, is electrically connected to a pipeline. Off-potential without IR-drop is measured with respect to a CSE by interrupting the steel and a pipeline. Recently, this method termed instant-off method has been widely used to assess cathodic protection conditions.

FIG. 10 shows a schematic of the method for measuring pipe-to-soil potential with a steel probe. In FIG. 10, no. 1 depicts a pipeline, no. 2 a steel probe, no. 3 a CSE, no. 4 an ammeter in line 5 between a pipeline and a steel probe, no. 6 an on/off switch, no. 7 a potentiometer in line 8 between a steel probe and a CSE, no.9 an electrode for cathodic protection, no. 10 an anode, no. 11 a sacrificial anode, no. 12 a recorder, respectively.

In the above mentioned system, the adequacy of cathodic protection is assessed by measuring on-potential (pipe-to-soil) potential, off-potential, and current density. On-potential and current density are simultaneously obtained before interruption of the steel probe and a pipeline. Off-potential is obtained after disconnection of the steel probe and a pipeline for 0.6 to 1.0 sec in every 10 to 20 sec by using an on/off switch 6. Time variations of on-potential, offpotential, and current density are recorded using a recorder 12. An example of the output data by the field study is shown in FIG. 11.

However, some issues regarding the above mentioned method arise as follows:

1̂ Original waveforms regarding on-and off-potentials, and probe currents are not obtained due to the use of a recorder with lowpass filter.

2̂ Off-potentials, DC and AC probe current densities are indispensable to assess the adequacy of cathodic protection. However, in the conventional method, off-potential of the steel probe is not accurately taken after disconnection of the steel probe and a pipe, when significant problem with depolarization is observed. Additionally, effective frequency in AC probe current density is not gained.

3̂ It is impossible to calculate data when the time averaged values are required, for example. Because digital on-and off-potentials, and DC and AC probe current densities are not acquired in the system.

To overcome the above mentioned issues 1̂ through 3̂, the inventor of this patent has proposed the invention relating to the Japanese Application No. 8-345313. The patent describes the evaluation method for cathodic protection of underground pipelines with a steel probe and a CSE near the pipeline at a depth, by numerically analyzing on-and off-potentials, and probe currents that are collected with use of a computer. The steel probe is electrically connected to a pipeline. Frequency analysis of collected data is performed, then levels of on-and off-potentials, and probe currents at effective frequencies are assessed.

Recently, buried pipelines tend to run parallel to electric transmission lines or railways. In such a case, a powerfill magnetic field is generated between a pipeline and ground, then a considerable voltage is induced particularly in a well coated pipeline. The above mentioned patent (No. 8345313) does not directly refer to data regarding AC corrosion.

On the other hand, it is the current situation that the buried environment of pipeline is aggravating the situation more and more in recent years and the situation is increasingly becoming the cause for AC corrosion.

SUMMARY AND OBJECTS OF THE INVENTION

The present invention is characterized in such a respect that it can provide AC (alternating current) corrosion counter-measures by burying the steel probe and a CSE adjacent to the cathodically protected pipeline and measuring simultaneously the on- and off-potential between the above mentioned steel probe and a CSE and DC (direct current) between the steel probe and the pipeline, and further by measuring the value of an AC between the steel probe and the pipeline in synchronism with this measurement by timing when evaluating the corrosion level from these values and evaluating the AC corrosion level from these values.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
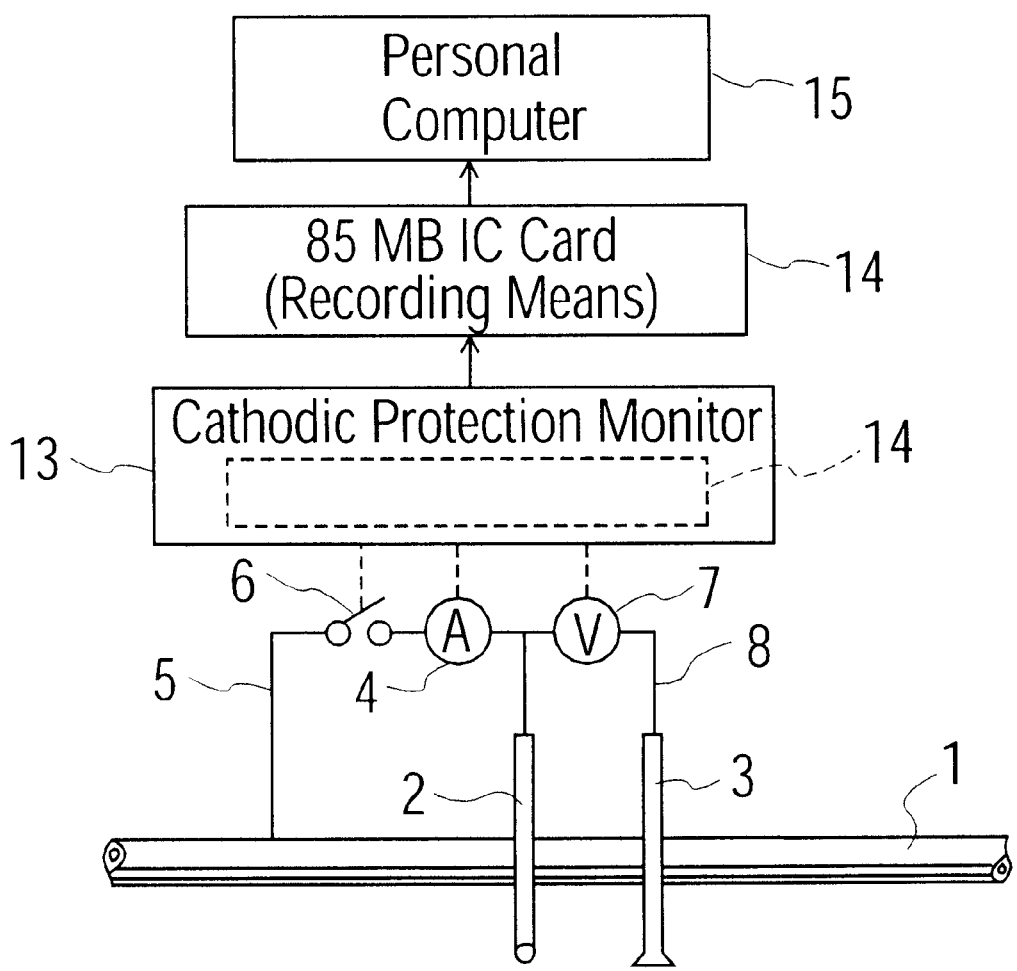
FIG. 1 is a diagram detailing a single test station of the present invention.

Referring to the drawings in particular, FIG. 1 shows a cathode protection unit relating to this invention, wherein no. 1 is a pipeline, no. 2 is a steel probe, no. 3 is a CSE, no. 4 is an ampere meter inserted into the line 5 connecting between the pipeline 1 and the probe 2, no. 6 is an ON/OFF switch, no. 7 is a voltage meter inserted into the line connecting between the probe 2 and the electrode 3. The DC power source for cathodic protection, the anode and the sacrificial anode are omitted in FIG. 1. No. 13 is a cathodic protection monitor, and an IC(integrated circuit) card (a recording means) (85 MB) 14 for recording the data is incorporated into this monitor 13, and saves the on-and off-potentials and probe current. And, this IC card 14 is set into a personal computer 15 for analyzing the obtained data.

Hereinafter, the acquisition of data and the analysis of these numerical data being conducted using the personal computer 15 are explained.

CATHODE PROTECTION DATA MEASUREMENT & ANALYSIS

Figure 2:
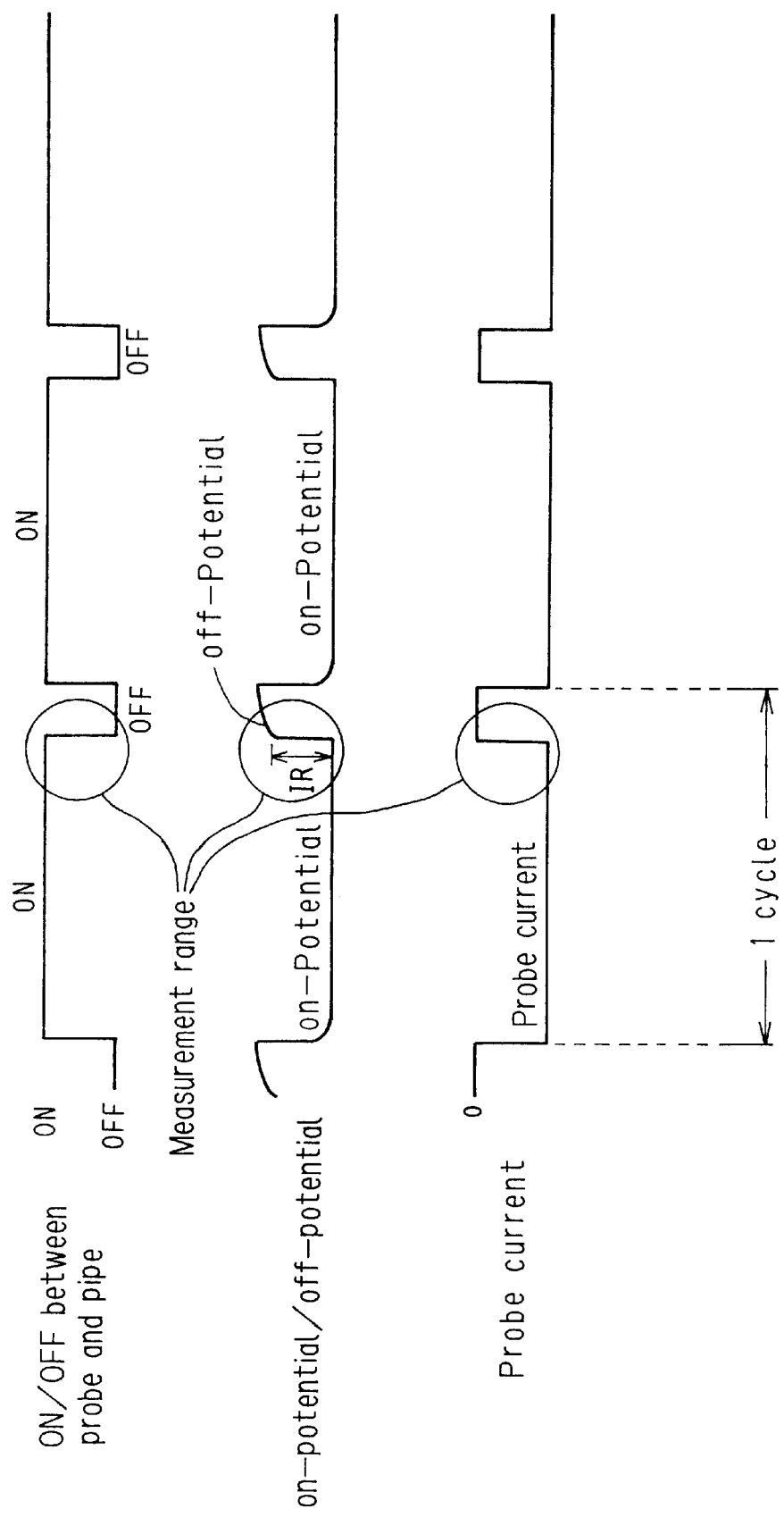
FIG. 2 is a schematic diagram representation of measuring time of on-potential, off-potential, and probe current.

As shown in FIG. 2, the measurement is taken for the data around the point of time when the probe 2 has changed from ON to OFF at all times. Generally, the ON time is very much longer than the OFF time, and basically the one cycle is set to 10 s with the ON time being 8.5 s (seconds) and the OFF time being 1.5 s. For example, if the measurement time is for 2 minutes, it means that 1 cycle has been repeated (i.e. more than one cycle per two minute measurement time). Basically, the time before OFF time and the time after the OFF time shall be set to 1 s. The range within the time before OFF and the time after OFF shall be sampled at every 0.1 ms for taking the values of on-potential, off-potential and probe current as finely as possible (For grasping the status as it is). Therefore, the number of each data of on-potential, off-potential and probe current becomes the voluminous quantity of as many as 120,000 data values.

1) Display of on-potential

Figure 3:
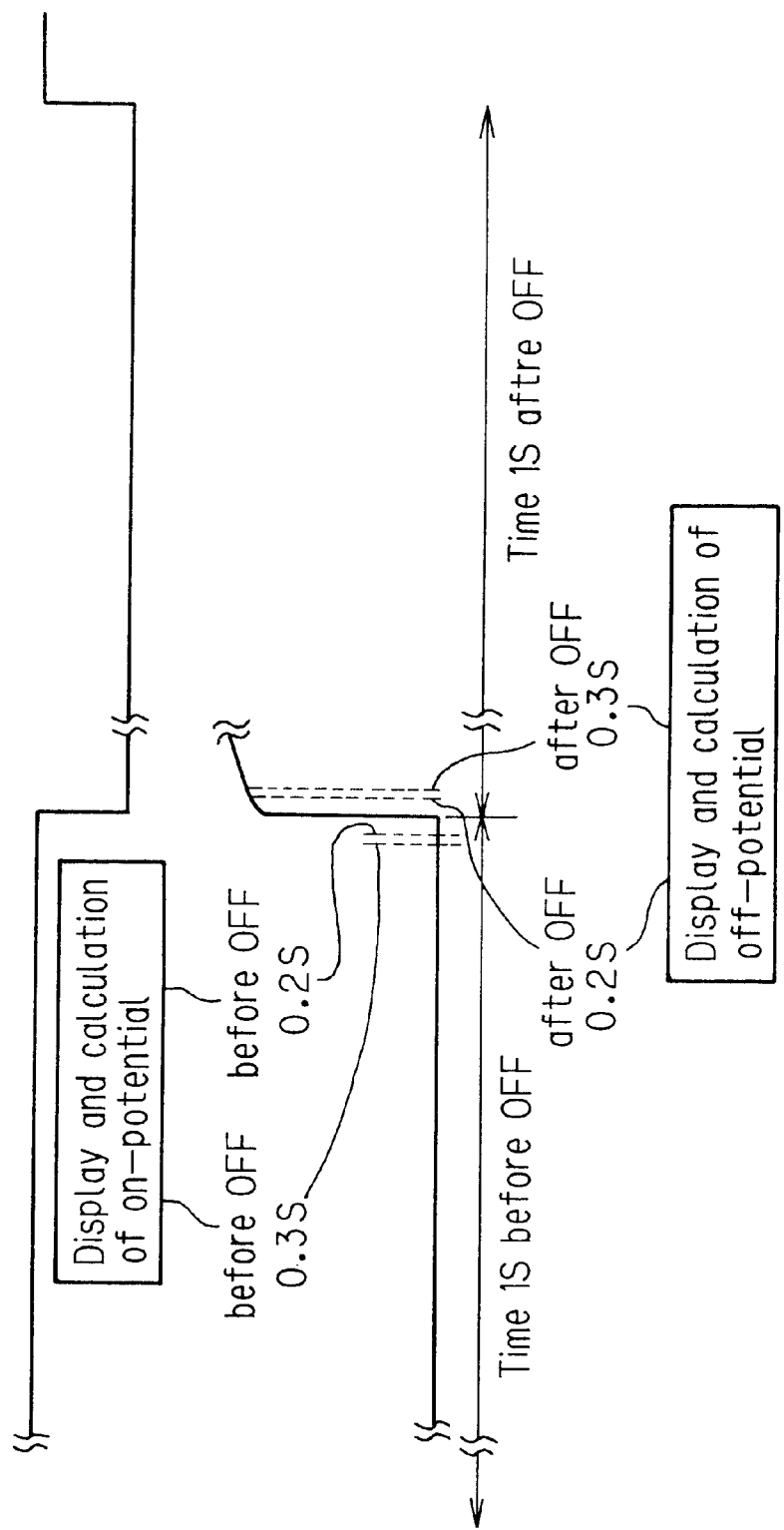
FIG. 3 is a diagram showing an explanatory view of a display and the calculation of on-and off-potentials.

Within the range of time before the preset OFF, the on-potential to the measuring instrument is displayed and calculated (maximum value, minimum value and averaged value). Empirically, the range from 0.3 s before OFF and 0.2 s is optimum for the display and calculation of on-potential (see FIG. 3). Therefore, because the time range of this 0.1 s is sampled at every 0.1 ms at one cycle, the total number of sampling becomes 1,000, and the maximum value, minimum value and averaged value in the 1,000 data are to be displayed.

2) Display of off-potential

Within the range of time after the preset OFF, the OFF potential to the measuring instrument is to be displayed and calculated. Theoretically, the off-potential is the probe potential subtracting the IR (mainly the protective current and soil resistance) immediately after the OFF, but because empirically an abnormal current signal is entered in many cases immediately after the OFF, the evaluation is made between the time range from 0.2 s to 0.3 s after the OFF. This becomes quite identical to the calculation of on-potential, which is to display the maximum value, minimum value and averaged value in 1,000 data at one cycle.

3) Display of probe current

Because the probe current is to be evaluated under the ON status, it becomes identical to the measurement of on-potential.

The displays of the on- and off-potentials and probe current can be optionally set so long as the range is within the time before OFF and the time after OFF.

SOFTWARE AND OUTPUT

For example, the measurement conditions shall be set as follows: (they are the standard ones):

ON time: 8.5 s

OFF time: 1.5 s 1 cycle: 10 s

Measurement time: 120 s

Time before OFF: 1 s

Time after OFF: 1 s

On-potential display measuring range: 0.3 to 0.2 s before OFF

Off-potential display measuring range: 0.2 to 0.3 s after OFF

Data sampling interval: 0.1 ms

Figure 4:
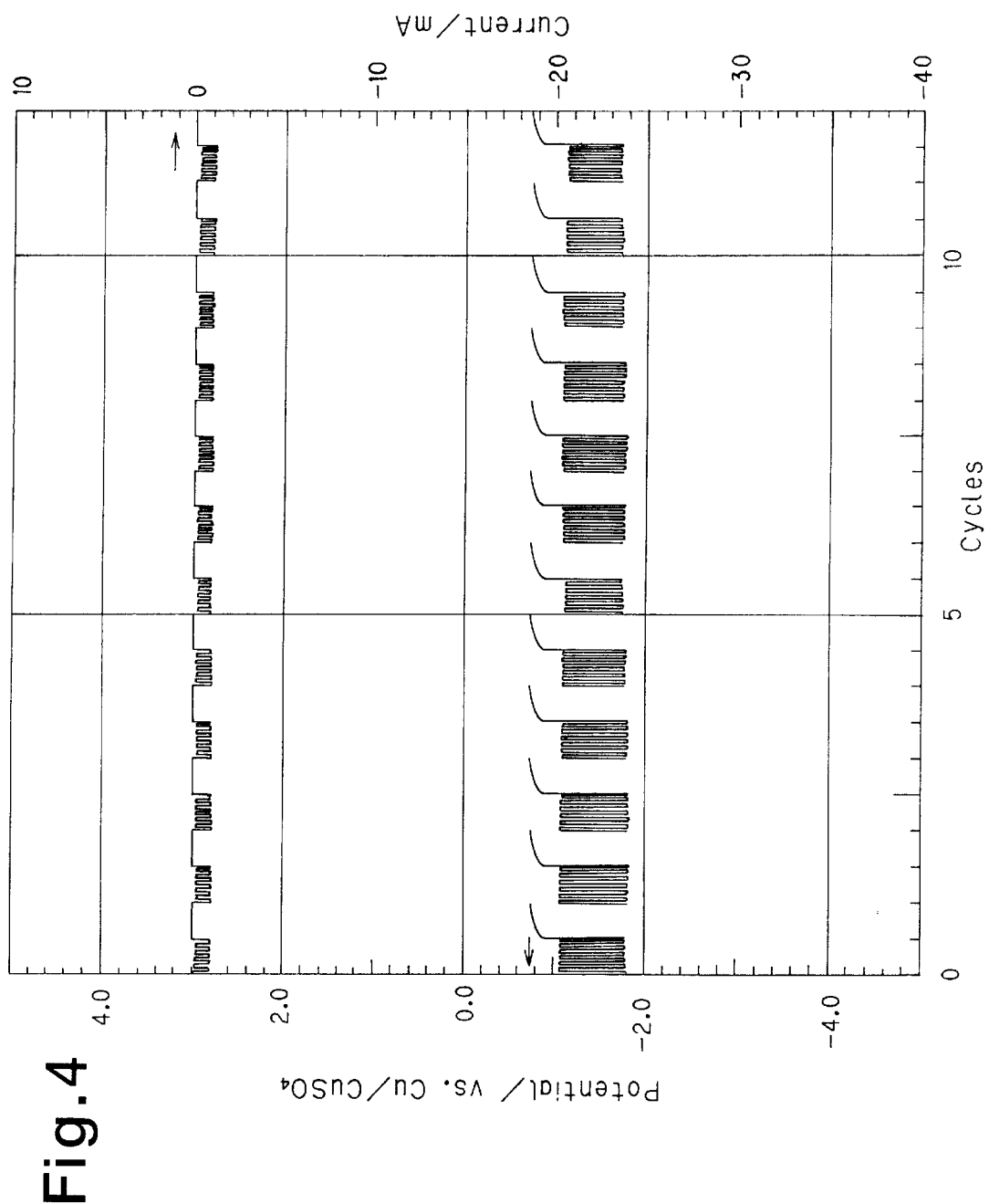
FIG. 4 is a diagram showing the behavior of potentials and currents.

Then, because the time before OFF and the time after OFF are identical to each other, 12 cycles can be obtained as the output as the embodiment in FIG. 4 shows with the OFF time between the probe 2 and the pipeline 1 as its target. The reason why each cycle is intermittent is because the continuous measurement is actually being conducted. The maximum value, minimum value and averaged value of on- and off-potentials and probe current within the present range are displayed to the right side of FIG. 4.

Figure 5:
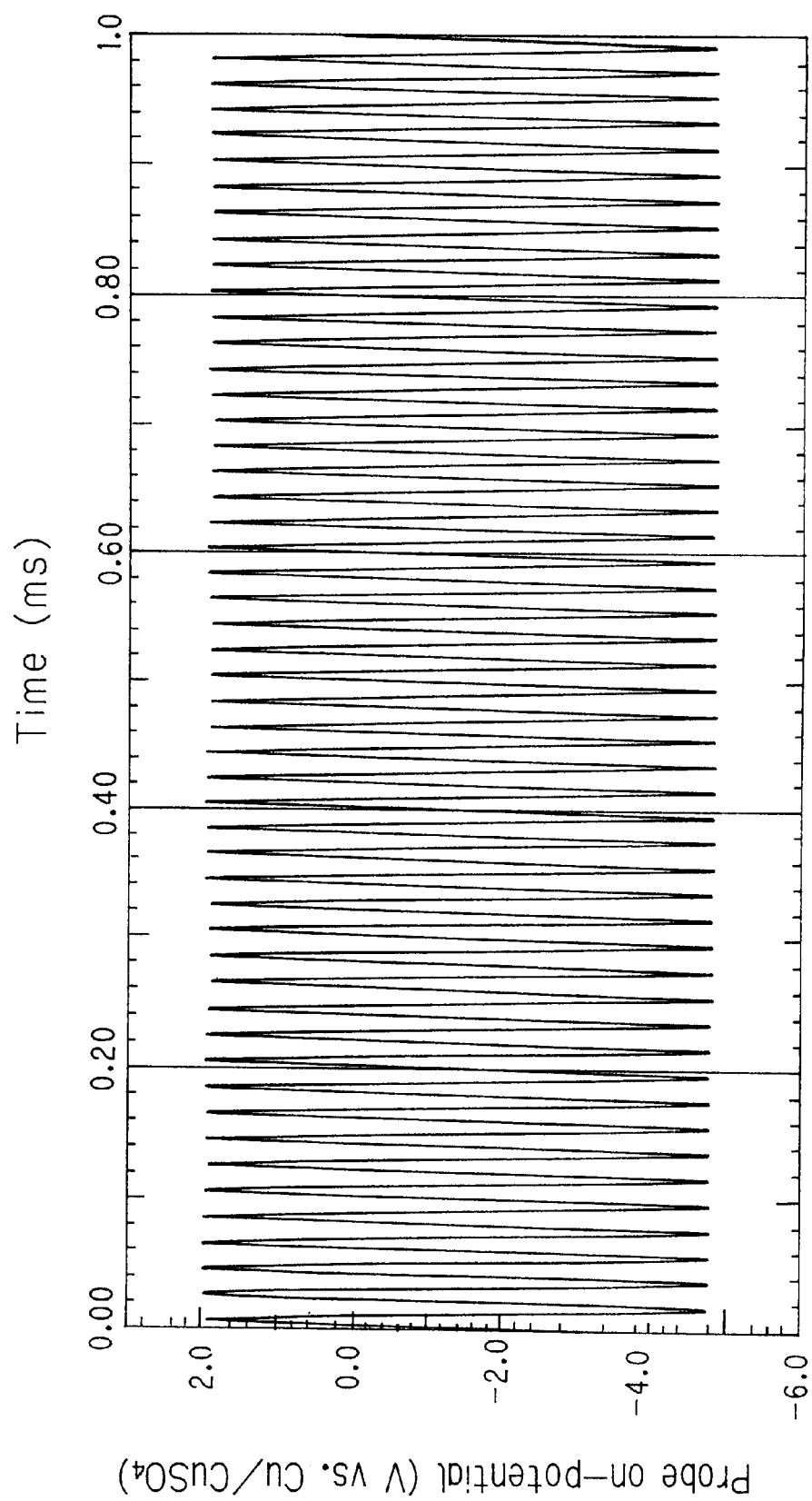
FIG. 5 is a diagram showing an explanatory view of the original wavefom of on-potential.
Figure 6:
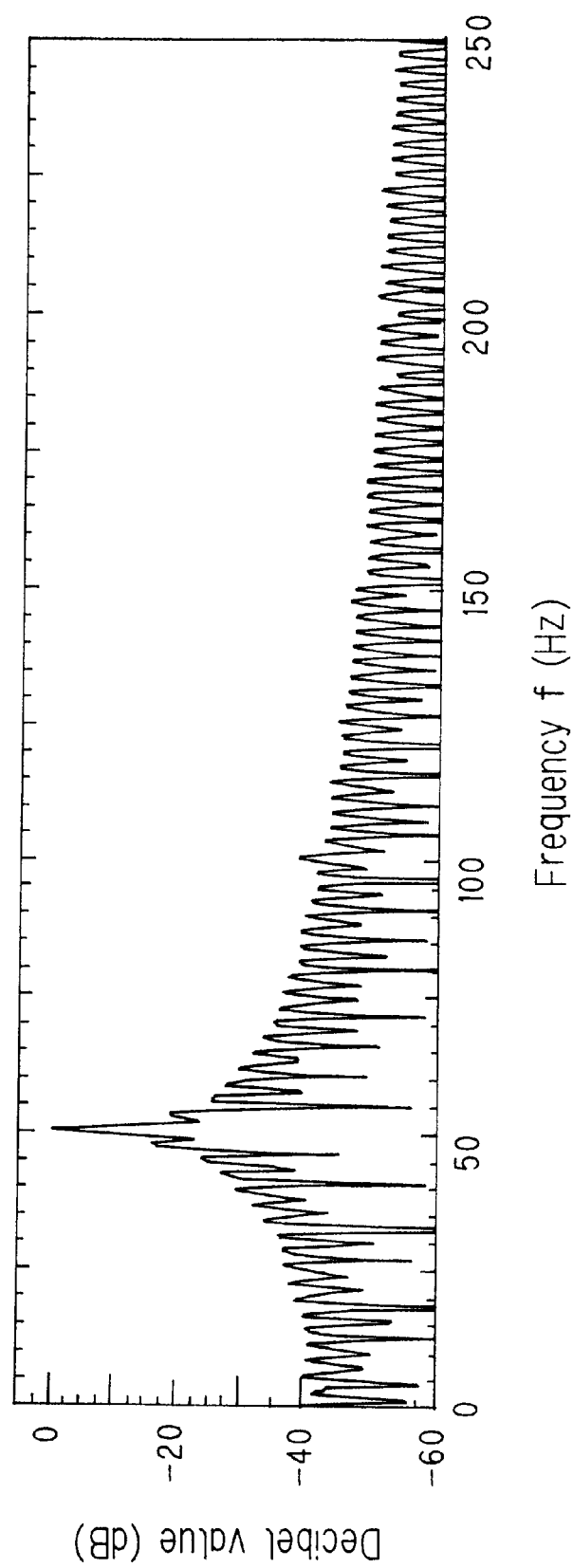
FIG. 6 is a diagram showing the behavior of on-potential and its spectrum.

The sampling interval is set to 0. 1 ms due to the following two reasons:

$\hat{1}$ By grasping the original waveforms of on-potential and probe current when the steel probe is electrically connected to a pipeline, the cause of fluctuation can be specified by the frequency analysis, and moreover, evaluation of the adequacy of cathodic protection is performed by the analysis of the original waveforms of on-potentials and probe currents. FIG. 5 is an explanatory view of the original waveform of on-potential while FIG. 6 displays in spectrum the analysis of on-potential by the FFT (Fast Fourier Transformation). Effectively only the 50 Hz component of the power-line frequency remains indicating the inductance of electric power transmission lines. What relates to the corrosion is the low frequency constituent out of the probe current taken at the same time with the on-potential.

Figure 7:
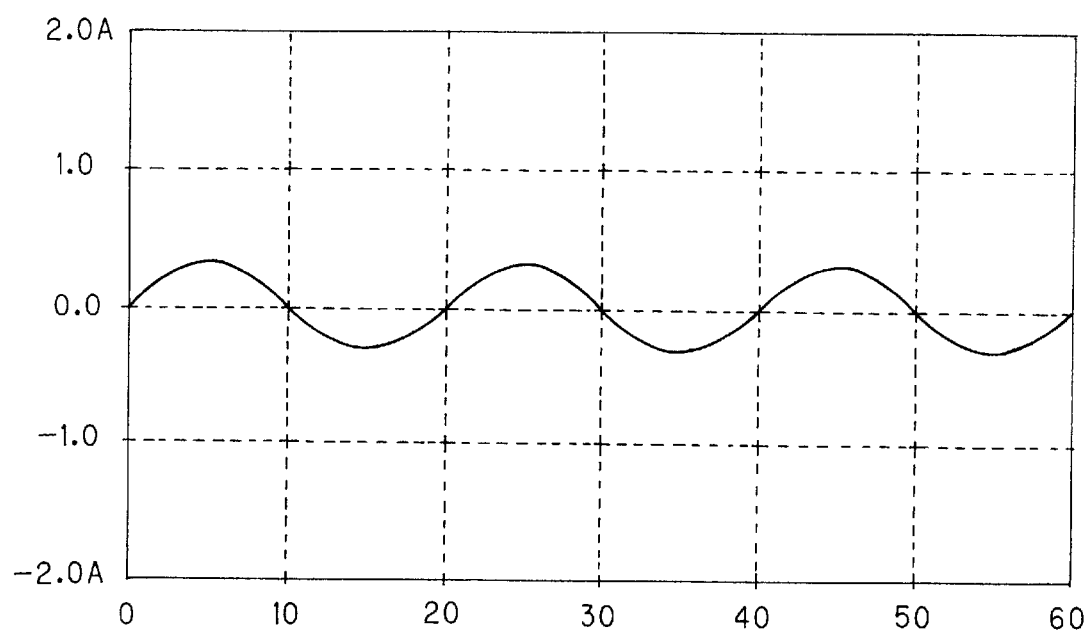
FIG. 7 is a diagram showing an example of probe current.

In the present embodiment, the inventor decided to treat the filter by the FFT based on the original wave form taken in 0.1 ms and calculate and display the averaged value of each constituent of 25 Hz, 50 Hz, 100 Hz, 200 Hz, and 500 Hz. FIG. 7 shows these embodiments.

$\hat{2}$ Probe off-potential must be determined on the basis of the analysis of original potential waveform. This is the reason why the data sampling time of 0.1 ms is required.

If the standard has not been satisfied in comparison with the following cathodic protection criteria as a result of analyzing the numerical value, the disposal for decreasing AC voltage should be taken by lowering the AC voltage of the pipeline and by connecting the low earth substance to the pipeline (it is predicted that the electromagnetic induction voltage is generated in the pipeline and AC corrosion may be induced).

CRITERIA FOR CATHODIC PROTECTION USING INSTANT-OFF METHOD WITH STEEL PROBES

1. Under conditions without induced AC voltage (a) at least- 1.0 V CSE off-potential, or (b) at least 0.010 mA/cm$^2$ DC probe current density 2. Under conditions with induced AC voltage Criteria for cathodic protection conditions with induced AC voltage have not yet been established. That is, the relationship between off-potential, DC probe cathodic current density, and AC probe current density is not well understood in order to prevent AC corrosion. However, positive proof that corrosion rate is suppressed below 0.010 mm/y has been obtained, when AC probe current density is lower than 5 mA/cm$^2$. Because of this situation, the tentative criteria for cathodic protection are presented; that is the above mentioned 1 and lower than 5 mA/cm$^2$ averaged AC probe current density.

The present inventory is to assess the adequacy of cathodic protection by evaluating DC components (on-potential, off-potential, and DC probe current density) together with AC probe current density.

Figure 8:
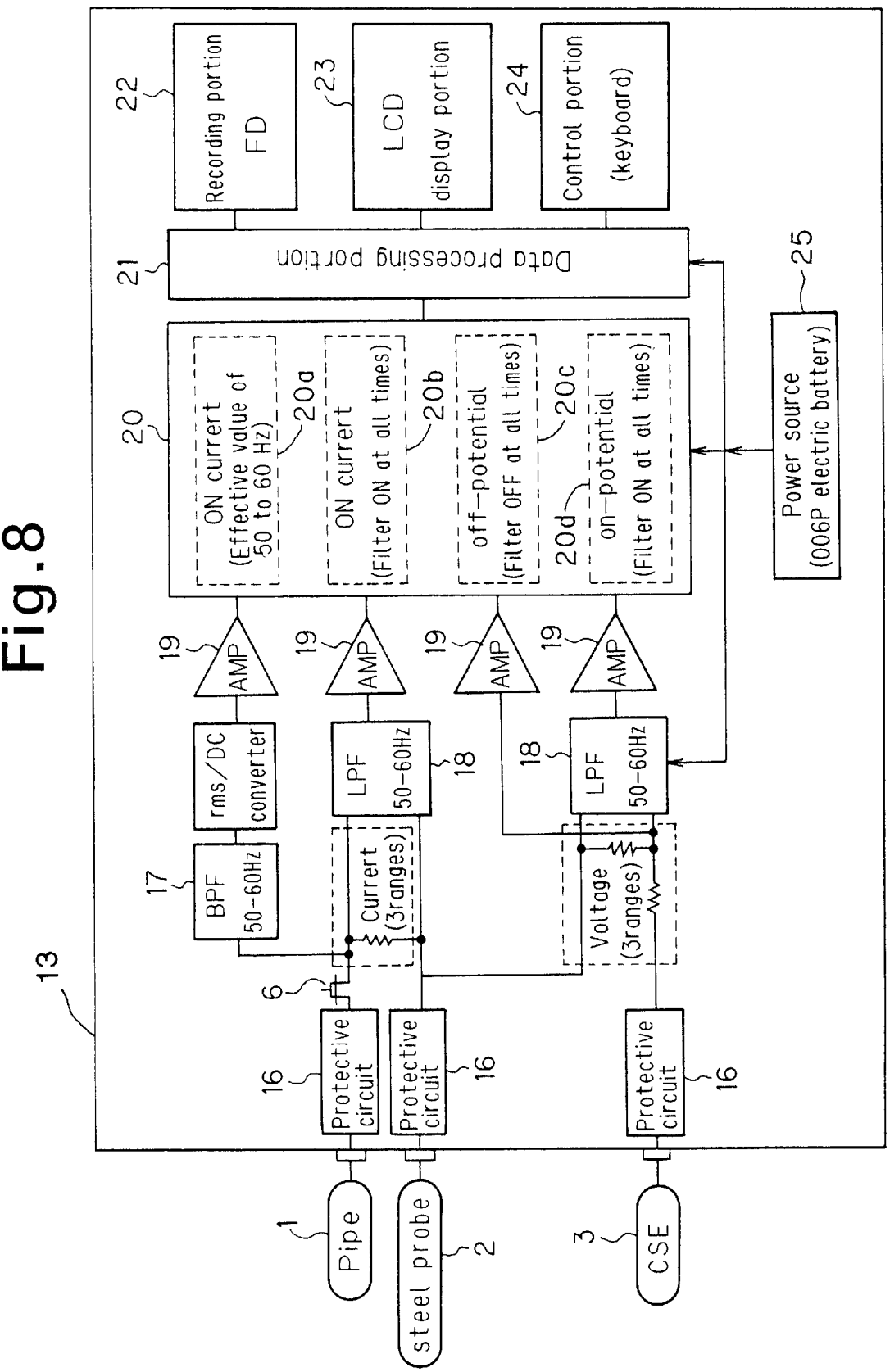
FIG. 8 is a circuit diagram showing an explanatory view of this invention.

This method (unit) is expounded on the basis of FIG. 8. In FIG. 8, no. 1 is a pipeline, no. 2 is a steel probe, no. 3 is a CSE, no. 6 is an ON/OFF switch, no. 13 is a cathodic protection monitor, no. 16 is a protective circuit, no. 17 is a band pass filter, no. 18 is a low pass filter, no. 19 is an amplifier, no. 20 is a measurement circuit, 20$a$ is an ON current (the effective value from 50 to 60 Hz zone) measuring portion, 20$b$ is an ON current (the filter is ON at all times) measuring portion, 20$c$ is an off-potential (the filter is OFF at all times) measuring portion, 20$d$ is an onpotential (the filter is ON at all times) measuring portion, 21 is a data processing portion, 22 is a recording portion, 23 is an LCD display, 24 is a control portion (keyboard) and 25 is a power source.

In this instrumentation, after the disconnection of the steel probe and a pipeline, potential data are collected at the sampling time of 0.1 ms without lowpass and bandpass filters. The reason why the presented procedures are taken is because 1) the potential fluctuation of the steel probe 2 is induced (it is imagined that the reason why there is a potential fluctuation is because the steel probe 2 is in a strong electromagnetic field) although the level of AC induction voltage is low even after the OFF under the overhead high voltage electric wire, and 2) there is the need for grasping the original waveform since there is the depolarization phenomenon of steel probe 2 after the OFF (the phenomenon where the steel probe 2 shifts toward nobler direction).

Figure 9:
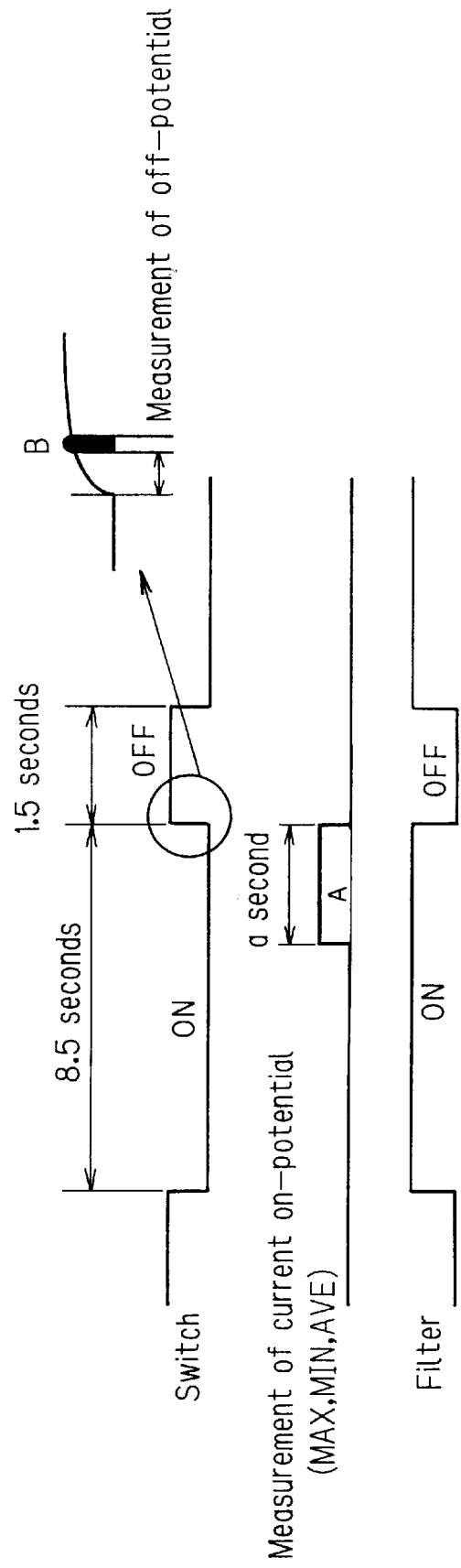
FIG. 9 is a diagram showing an explanatory view of measurement method of the present invention.
Figure 10:
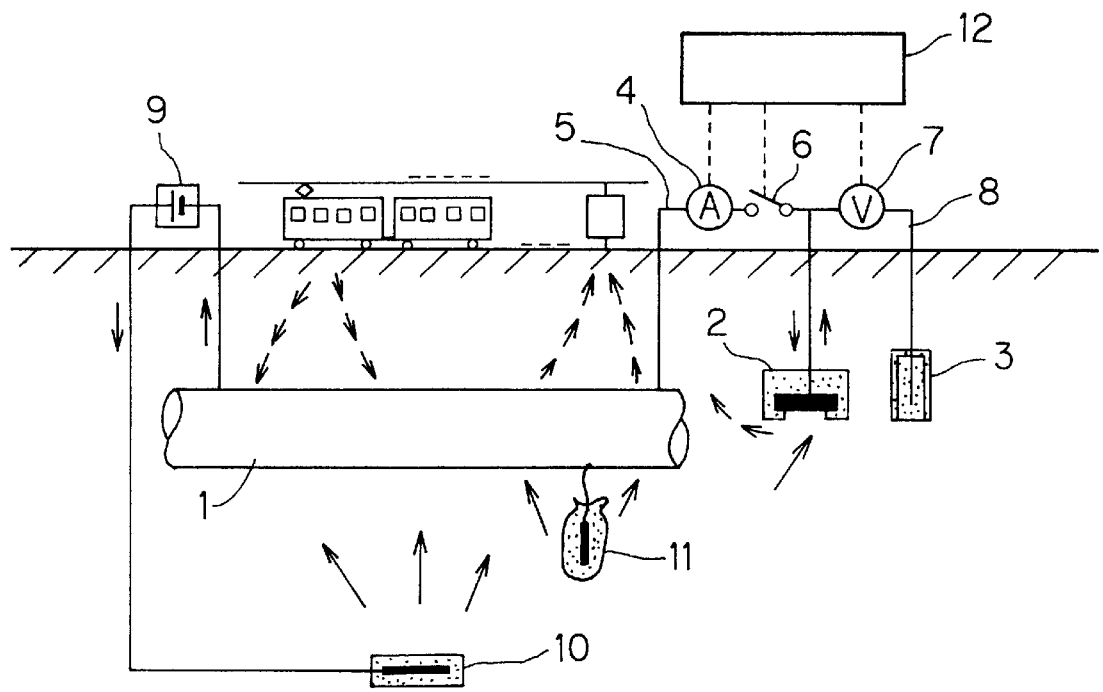
FIG. 10 is an explanatory view of a cathode protection system.
Figure 11:
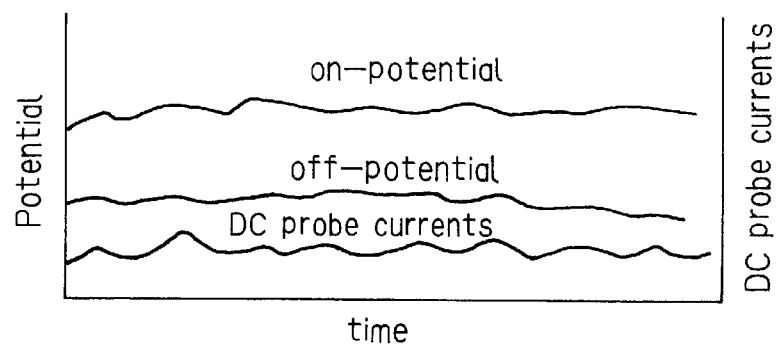
FIG. 11 is a diagram showing an example of a recorder output of cathode protection data of the system of FIG. 10.

FIG. 9 shows an explanatory view of the measurement method for estimating AC corrosion level with a steel probe interrupted at a cycle of 8.5-second on and 0.5-second off by using an ON/OFF switch 6, which is repeated for 120 seconds.

During this ON/OFF state, the maximum value, minimum value and averaged value of probe on-potential and DC probe current is measured with the low pass filter 18 (cut-off frequency of 50 Hz) ON, and moreover the rms current of probe AC 50/60 Hz shall be measured with the band pass filter 17 ON, and further the probe off-potential (the averaged value of 0.1 ms sample data) shall be measured with the filter being OFF).

Symbol "A" in FIG. 9 is the maximum, minimum and averaged value measurement (the probe rms current of on-potential, DC 50/60 Hz), and Symbol "B" is the averaged value of 0.1 ms sample data, whose start and end can be freely designated at the control portion 24.

The matter was measured 90 cycles for 15 minutes for both the "A" and "B" cases at a test station.

The timing of 8.5 seconds for ON time and 1.5 seconds for OFF time is for not disturbing the influence of electric iron operation against the pipeline 1 (from the study result in the field thus far). However, in the case of overhead electric power transmission lines, on- and off-time does not have a significant meaning due to repeatable phenomena.

As described above, the present invention enables an engineer to evaluate the effect of induced AC voltage on a pipeline paralleling an electric power transmission line or a railway. Thereby, the pipeline integrity for cathodic protection will be ensured.

While specific embodiments of the invention have been shown and described in detail to illustrate the application of the principles of the invention, it will be understood that the invention may be embodied otherwise without departing from such principles.

What is claimed is:

1. A method to assess the adequacy cathodic protection conditions of a cathodically protected pipeline, the method comprising the steps of:

burying a steel probe and a saturated copper/copper sulfate reference electrode (CSE) adjacent to the cathodically protected pipeline;

electrically connecting the steel probe and the pipeline via an ON/OFF switch;

electrically connecting the steel probe and the CSE;

simultaneously measuring probe on-potential, probe off-potential, probe DC current density and probe AC current density;

using a low pass filter when measuring the probe DC current densities to form data corresponding to a low frequency constituent of the probe current;

using a band pass filter when measuring the probe AC current density to form data only corresponding to a constant frequency band constituent of the probe current;

when measuring probe off-potential, measuring probe potential with respect to the CSE after switching off between the probe and the pipeline at a constant time interval and obtaining the average data of these potential values;

evaluating the DC corrosion level from probe off-potential and the probe DC current density; and evaluating the AC corrosion level from the probe off-potential and probe AC current density.

2. A system to assess the adequacy of cathodic protection conditions of a pipeline using a steel probe, the unit comprising:

a device for evaluating the DC corrosion level with a steel probe and a saturated copper/copper sulfate reference electrode (CSE) to be buried adjacent to the cathodically protected pipeline, cables connected between the pipeline and the steel probe and between the steel probe and the CSE, an ON/OFF switch and an ammeter between the pipeline and the steel probe and a potentiometer between the steel probe and the CSE, whereby simultaneous measurement may be made of on/off potentials between the steel probe and the CSE and of DC current densities between the steel probe and the pipeline by switching on and off, and for evaluating the DC -corrosion level from the obtained values;

AC current density measuring means for measuring the AC current densities between the said steel probe and pipeline in synchronization with measuring timing of criteria means of the said DC corrosion level;

a means for taking in only the low frequency constituent of probe current using a low pass filter in case of the probe DC current densities and for taking in only the constant frequency band constituent of probe current using a band pass filter in case of AC current densities when measuring the DC current densities between the said probe and pipeline and the AC current densities and probe off-potentials between the probe and CSE;

a probe off-potential measuring means for measuring the potential values of the probe with respect to the CSE at a constant time intervals and for obtaining an average value of these values when measuring probe off-potentials; and a criteria means of AC corrosion level for evaluating AC corrosion level from the said AC current densities and probe off-potentials.

3. A method to assess the adequacy cathodic protection conditions of a cathodically protected pipeline, the method comprising the steps of:

burying a steel probe and a saturated copper/copper sulfate reference electrode (CSE) adjacent to the cathodically protected pipeline, electrically connecting the steel probe and the CSE;

during a measuring timing cycle, using the switch to electrically connect and disconnect the steel probe and the pipeline, to provide a measurement timing cycle with the steel probe and the pipeline electrically connected to the pipeline for probe on-potential, and after with the steel probe and the pipeline electrically disconnected for probe off-potential;

during each measurement timing cycle measuring probe on-potential, probe off-potential, probe DC current density and probe AC current density;

using a low pass filter to form filtered DC current density data from the measured probe DC current density, corresponding to a low frequency constituent of the probe current;

using a band pass filter to form filtered AC current density data from the measured probe AC current density, corresponding to a constant frequency band of the probe current;

said probe on-potential and said probe off-potential being potential values measured with respect to the CSE at constant time intervals during each measurement timing cycle;

forming average data from said potential values as the probe off-potential;

evaluating the DC corrosion level from the probe off-potential and the DC current densities and, evaluating the AC corrosion level from the probe off-potential and the AC current densities.

4. The method according to claim 3, wherein the filtered DC current density data, is formed using a low pass filter of 50–60 Hz, wherein the constituent of the probe current measured, which is lower in frequency than 50–60 Hz is regarded as the probe DC current and the DC current density data is obtained by dividing this value by the probe area.

5. The method according to claim 3, wherein the filtered probe AC current density data, is formed using a band pass filter of 50–60 Hz, the AC current density is obtained by dividing this value by the probe area.

6. The method according to claim 3, wherein the measurement of the probe potentials to obtain the probe off-potential takes place from 0.2 seconds to 0.3 seconds after switching off the probe and pipeline to avoid abnormal electric signals.

7. The method according to claim 3, wherein the probe potential with respect to the CSE are measured at an intervals of 0.1 ms after switching off, over than one cycle of 50 Hz or 60 Hz and the values measured from the intervals are averaged to form the probe off-potential.

* * * * *